(12) United States Patent
Dion (10) Patent No.: US 7,041,080 B2
(45) Date of Patent: May 9, 2006

(54) ROTARY VALVE FOR BALLOON CATHETER

(75) Inventor: Gregory R. Dion, Lynn, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 213 days.

(21) Appl. No.: 10/633,433

(22) Filed: Aug. 1, 2003

(65) Prior Publication Data

US 2005/0027246 A1    Feb. 3, 2005

(51) Int. Cl.
*A61M 29/00*    (2006.01)

(52) U.S. Cl. .............................. 604/99.02; 604/99.04; 604/97.01

(58) Field of Classification Search ............... 604/48, 604/93.01, 97.01, 99.02, 99.03, 99.04, 167.03, 604/236, 248, 32, 500, 509, 510, 99.01, 246, 604/167.05; 606/194; 251/309–311
See application file for complete search history.

(56) References Cited

U.S. PATENT DOCUMENTS

| | | | | |
|---|---|---|---|---|
| 3,726,282 A | * | 4/1973 | Patel | 604/99.02 |
| 4,026,298 A | * | 5/1977 | Grausz | 604/249 |
| 4,429,856 A | * | 2/1984 | Jackson | 251/149.1 |
| 4,850,350 A | * | 7/1989 | Jackson | 128/207.16 |
| 5,399,172 A | * | 3/1995 | Martin et al. | 604/248 |
| 5,472,432 A | * | 12/1995 | Martin | 604/248 |
| 5,728,064 A | | 3/1998 | Burns et al. | |
| 6,050,972 A | * | 4/2000 | Zadno-Azizi et al. | 604/97.01 |
| 6,090,083 A | * | 7/2000 | Sell et al. | 604/249 |
| 6,355,014 B1 | | 3/2002 | Zadno-Azizi et al. | |
| 6,368,317 B1 | * | 4/2002 | Chang | 604/544 |
| 6,475,185 B1 | * | 11/2002 | Rauker et al. | 604/96.01 |
| 6,500,166 B1 | | 12/2002 | Zadno-Azizi et al. | |
| 6,544,276 B1 | | 4/2003 | Zadno-Azizi et al. | |
| 6,743,208 B1 | * | 6/2004 | Coyle | 604/164.13 |
| 2002/0133117 A1 | | 9/2002 | Zadno-Azizi et al. | |
| 2003/0004461 A1 | | 1/2003 | Kupiecki | |

* cited by examiner

*Primary Examiner*—Nicholas Lucchesi
*Assistant Examiner*—Theodore J. Stigell
(74) *Attorney, Agent, or Firm*—James F. Crittenden (57) ABSTRACT

A rotary valve for a balloon catheter, including a hollow guidewire with a central lumen and a portion of a rotary shaft disposed within a guidewire proximal end. Rotating the rotary shaft of the rotary valve controls flow of an inflation fluid into and through the guidewire central lumen.

9 Claims, 8 Drawing Sheets

ROTARY VALVE FOR BALLOON CATHETER

FIELD OF THE INVENTION

This invention relates generally to balloon catheters and guidewire deployment of catheter-based treatment devices. More specifically, the invention relates to a balloon catheter with a rotary valve mechanism.

BACKGROUND OF THE INVENTION

Balloon catheter and guidewire-deployed treatment systems are used to temporarily occlude a vessel in the coronary vasculature during diagnostic and interventional procedures. Guidewires help guide the insertion of catheters and various medical instruments to a desired treatment location within the vasculature of a human body. A flexible guidewire can be advanced through the blood vessels until the guidewire extends across the vessel segment to be treated. Treatment catheters, such as a balloon dilation catheter for PTCA, may be inserted over the guidewire and similarly advanced through the vasculature until they reach the treatment site.

Balloon angioplasty is commonly used to alleviate stenotic lesions in blood vessels, thereby reducing the need for heart bypass operations. Medical balloon catheters also have been proven efficacious in treating a wide variety of blood vessel disorders such as intravascular restrictions due to atherosclerosis or restenosis.

Vascular stenoses, which may be partially or totally occluded, are often characterized by having a mineral component. A variety of different protocols have been developed for treating vascular diseases with these calcified areas. The treatment methodologies generally involve mechanically removing or reducing the size of the stenosis, mechanical debridement, atherectomy, balloon angioplasty, stenting, and bypass surgery procedures.

Intravascular procedures often use one or more catheters, such as balloon catheters to dilate vascular restrictions or atherectomy catheters to remove the restriction. Unfortunately, the intravascular procedures associated with these devices may result in particles being dislodged while the restriction is dilated or cut. Such dislodged particles may move downstream from the area of restriction, possibly causing an embolism, which could compromise the flow of blood to the surrounding tissue.

Treatment procedures using occlusion balloon catheters and aspiration catheters have been developed to help prevent potentially embolic debris from migrating with the blood stream. The occlusion balloon catheter blocks or impedes blood flow while the aspiration catheter aspirates and removes embolic particles from the area of the stenosis.

Some catheter treatment procedures introduce and remove sequentially a number of treatment catheters over a guidewire, the latter acting as a guide for the exchange of one treatment catheter to another. Embolic containment procedures typically employ one or two occlusion balloons in conjunction with an aspiration catheter. One example of an inflatable occlusion catheter includes an occlusion balloon mounted distally on an elongated wire-like shaft that extends through a guidewire lumen of a primary dilation or atherectomy catheter. The balloon is advanced through a vessel, positioned distal to the site of the stenosis, and temporarily inflated to prevent embolic particles from migrating downstream as the occlusive restriction is being dilated or cut. After the restriction has been treated, the primary treatment catheter can be removed from over the guidewire of the occlusion balloon catheter. An aspiration catheter can then be advanced to the treatment site to aspirate any embolic debris generated during the treatment. Once the embolic particles have been aspirated, the occlusion balloon(s) is/are deflated and removed from the patient.

An occlusion catheter is often constructed as a guidewire having a hollow shaft, a flexible, shapeable distal tip, and a deflated elastomeric occlusion balloon attached at the proximal end of the distal tip. During use, the distal tip of the guidewire and the balloon cross the lesion, an inflation device is attached to the proximal end of the catheter, and the occlusion balloon is inflated with dilute contrast agent. Following the inflation of the balloon, an angiogram using fluoroscopy may be taken to ensure complete occlusion by the balloon.

The occlusion guidewire can be used in coordination with other treatment catheters to infuse or deliver fluoroscopic material and therapeutic agents to the treatment site. With the occlusion balloon inflated, balloon angioplasty or stenting may be performed. A handheld inflation device can be removed from the proximal end of the catheter while the occlusion balloon remains inflated, and then a stent-delivery catheter may be exchanged to provide a percutaneous transluminal angioplasty. The embolic particles that are released during a coronary angioplasty or stenting procedure may remain upstream of the inflated occlusion balloon. Following the removal of the angioplasty balloon catheter or stent-delivery catheter, an aspiration catheter may be introduced over the occlusion guidewire to aspirate the particles.

A specific example of an occlusion catheter is described by Rauker and others in "Occlusion Device", U.S. Pat. No. 6,475,185 issued Nov. 5, 2002. The occlusion device includes an elongated tubular shaft having an inflatable balloon disposed near the distal end of the elongate shaft with a proximal seal of a sufficiently small profile to allow a second catheter to pass over the distal occlusion device while the inflatable balloon remains uninflated. One occlusion device includes an elongated fluid displacement rod within the elongated shaft of the occlusion device, providing both a fluid pressure source and a seal.

Currently used occlusion balloon catheters are able to control the flow of inflation and contrast fluid with sealing members such as plugs or valves located on the proximal end of the catheter. An exemplary catheter valve is a plug consisting of a wire that is formed to provide friction in a hollow guidewire or hypotube with a sealing member on the distal end of the wire. The plug is pushed in and out, which moves the sealing member distal and proximal to an inflation port via frictional pads at the proximal end of the catheter that grip the plug wire. The pads may be moved in conjunction with an adapter knob that is positioned on the hypotube. The inflation port of the hypotube is positioned to line up with the inflation port on the adapter to provide a continuous fluid path to inflate the occlusion balloon. Fluid is transferred through the hypotube to fill the occlusion balloon.

Manufacturers of balloon catheters have developed several types of sealing mechanisms used to control the flow and seal inflation fluid into the occlusion balloon. Sell and others have used a valve of an inner tube that is closely fit into an outer tube, as disclosed in "Low Profile Valve and Balloon Catheter", U.S. Pat. No. 6,090,083 issued Jul. 18, 2000. The low-profile inflation valve includes a first thermoplastic tube with at least one region of decreased inner diameter, and a structure, which may be a tube, movably located inside the lumen. The region of decreased inner diameter of the first tube forms a seal with a portion of the structure.

Improvements to a valve for a balloon occlusion catheter are proposed in "Low Profile Catheter Valve and Inflation Adaptor", Zadno-Azizi et al., U.S. Patent Application 2002/0133117 published Sep. 19, 2002; "Exchange Method for Emboli Containment", Zadno-Azizi et al., U.S. Pat. No. 6,544,276 issued Apr. 8, 2003; "Method of Emboli Protection using a Low Profile Catheter", Zadno-Azizi et al., U.S. Pat. No. 6,500,166 granted Dec. 31, 2002; and "Low Profile Catheter Valve", U.S. Pat. No. 6,355,014, Zadno-Azizi et al., granted Mar. 12, 2002. The catheter includes a low-profile catheter valve with a movable sealer portion positioned within the inflation lumen of a catheter. The sealer portion forms a fluid tight seal with the inflation lumen by firmly contacting the entire circumference of a section of the inflation lumen. The sealer portion is positioned proximate to a side-access inflation port on the catheter, establishing an unrestricted fluid pathway between the inflation port and an inflatable balloon on the distal end of the catheter. The sealer portion can be moved to a position distal of the inflation port, thereby preventing fluid from being introduced into or withdrawn from the balloon via the inflation port. An inflation adaptor can be used for moving the sealer portion within the catheter to establish or close the fluid pathway between the inflation port and the inflatable balloon.

A related low-profile catheter valve comprising a movable sealer portion positioned within the inflation lumen of a catheter is described in "Guidewire Inflation System", Zadno-Azizi et al., U.S. Pat. No. 6,050,972 granted Apr. 18, 2000. The sealer portion forms a fluid tight seal with the inflation lumen by firmly contacting the entire circumference of a section of the inflation lumen. The sealer portion may be positioned proximally of a side-access inflation port on the catheter to establish an unrestricted fluid pathway between the inflation port and an inflatable balloon on the distal end of the catheter. The sealer portion can be moved to a position distal of the inflation port, thereby preventing any fluid from being introduced into or withdrawn from the balloon via the inflation port. In one of the embodiments of the catheter valve, a tubular sealing member is used as a rotary valve mechanism at the distal end of the catheter. The tubular sealer fits tightly within the lumen of the catheter and may rotate within the lumen. Fluid flows through the valve when the tubular sealer rotates within the lumen to align its opening or port to the side-port access of the lumen.

Another description of a valved balloon catheter having a wire with a valve plug slidably disposed within the inflation lumen is described in "Balloon Catheter with Delivery Side Holes", Kupiecki, U.S. Patent Application 2003/0004461 published Jan. 2, 2003. The valve plug forms an adjustable pressure seal at a valve seat on the distal end of the catheter and allows fluid within the inflation lumen to be pressurized by a fluid source in order to facilitate balloon inflation.

Recent research continues to address the need for an improved valve system with more control over fluid flow to and from an occlusion balloon positioned within a vessel in a body. The desirable valve has a more reliable sealing member that does not require careful alignment of a sealer portion of a valve with small inflation holes in a hypotube. The desirable valve also does not require hard-to-control axial movement of the sealer portion during actuation. Therefore, an improved valve for a balloon catheter system is desirable for catheter-employed treatments for vessels in the body, providing greater control of fluid through a catheter, and increased utility and performance of associated medical devices used during the treatment of vascular conditions.

SUMMARY OF THE INVENTION

One aspect of the invention provides a rotary valve for a balloon catheter, including a hollow guidewire having a central lumen and a portion of a rotary shaft disposed within a proximal end of the hollow guidewire. Turning the rotary shaft of the rotary valve controls the flow of inflation fluid through the central lumen of the hollow guidewire.

Another aspect of the invention is a system for treating a vessel in a body. The vessel treatment system includes a hollow guidewire having a central lumen, an inflatable balloon attached adjacent to a distal end of the hollow guidewire, and a rotary valve including a portion of a rotary shaft disposed within a proximal end of the hollow guidewire. Turning the rotary shaft of the rotary valve controls flow of an inflation fluid through the central lumen of the hollow guidewire and into an interior region of the inflatable balloon.

Another aspect of the invention is a method of operating a balloon catheter. A portion of a rotary shaft extending within a hollow guidewire is rotated, and in response to the turning of the rotary shaft, an inflation hole is opened. Fluid is injected through the open inflation hole, into and through the hollow guidewire, and into an inflatable balloon in communication with the hollow guidewire.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein.

The drawings are not to scale.

DETAILED DESCRIPTION OF THE PRESENTLY PREFERRED EMBODIMENTS

Figure 1:
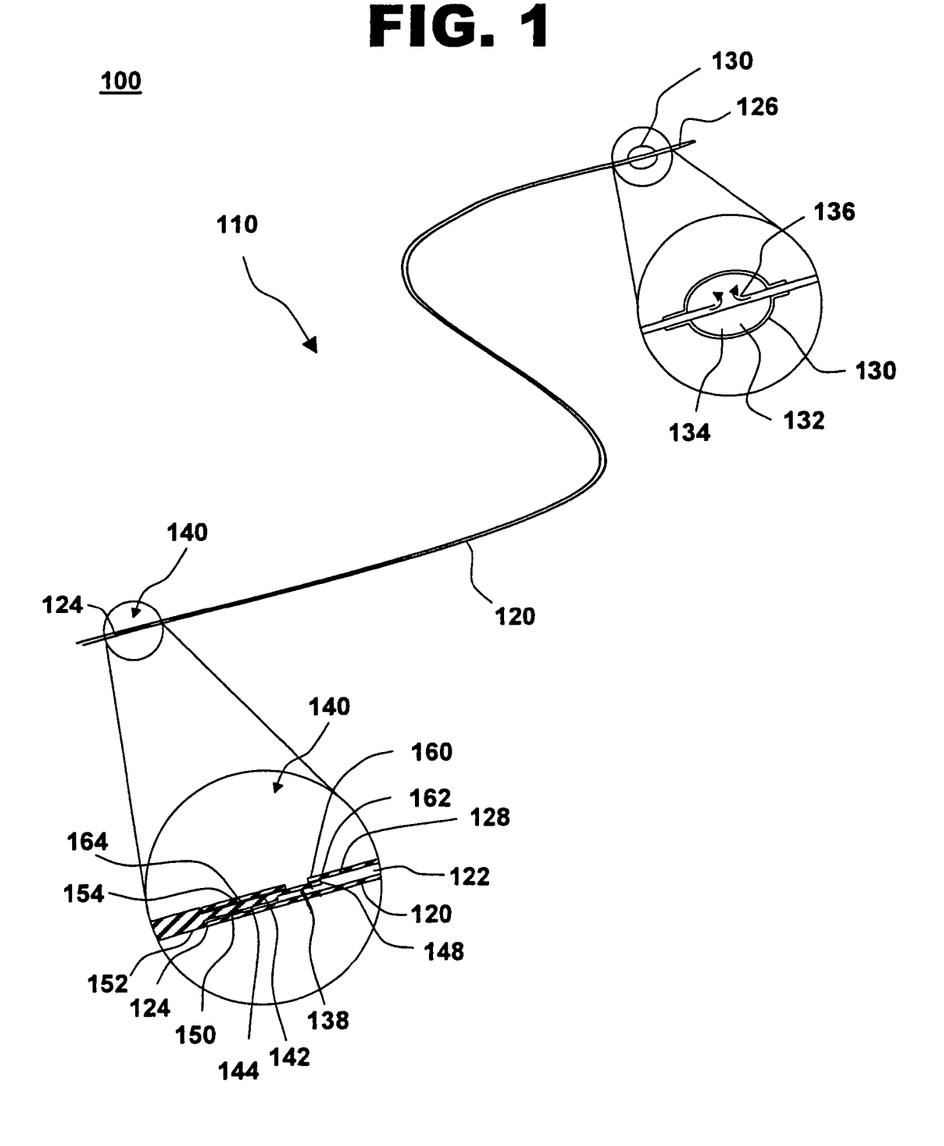
FIG. 1 is an illustration of a system for treating a vessel in a body, in accordance with one embodiment of the current invention.

FIG. 1 illustrates a system for treating a vessel in a body, in accordance with one embodiment of the present invention at 100. Vessel treatment system 100 includes balloon catheter 110 with hollow guidewire 120 having central lumen 122. Hollow guidewire 120 has proximal and distal ends 124, 126, respectively. Inflatable balloon 130 is attached near guidewire distal end 126. Balloon catheter 110 includes rotary valve 140 with a first portion 150 of rotary shaft 142 disposed within guidewire proximal end 124. Flow of inflation fluid 132 through guidewire central lumen 122 and into interior region 134 of inflatable balloon 130 is controlled by rotating rotary shaft 142.

Vessel treatment system 100, when inserted into the body, may be used as a temporary occlusion device for blocking fluid flow through arteries or veins. In another application, vessel treatment system 100 is used as a dilation catheter whereby blood vessel stenoses may be enlarged by inflating balloon 130. In other applications, vessel treatment system 100 is used in coordination with other treatment catheters, such as a stent-deployment catheter, an aspiration catheter, an inspection catheter, a measurement catheter, an angioplasty catheter, an atherectomy catheter, a drug-delivery catheter, an ultrasound device, a laser catheter, an imaging catheter, or a therapy catheter. Treatment of vascular conditions may include the prevention or correction of various ailments and deficiencies associated with the cardiovascular system, the cerebrovascular system, urogenital systems, biliary conduits, abdominal passageways and other biological vessels within the body.

When balloon catheter is 110 deployed, guidewire distal end 126 is inserted into the body and directed through the vasculature until guidewire distal end 126 is positioned at the desired location. In one example, balloon catheter 110 is inserted through a needle puncture in a femoral artery. When positioned, inflatable balloon 130 is inflated, blocking flow through the vessel and possibly temporarily anchoring inflatable balloon 130 to the vascular wall. Long, flexible, small-diameter hollow guidewire 120 may then be used to guide treatment catheters to the desired treatment site. In one example, an over-the-wire treatment catheter is delivered. In another example, a rapid exchange approach is used, as will be understood by those of skill in the field of catheterization.

Hollow guidewire 120 may be formed, for example, from an extruded or welded tubular material such as nitinol, stainless steel, or other suitable tubing material. In one example, hollow guidewire 120 has an outer diameter of 0.014 inches and an inner diameter on the order of 0.009 inches, with a length between 135 centimeters and 300 centimeters. The length of hollow guidewire 120 may be on the order of 300 centimeters, allowing over-the-wire (OTW) catheters to be inserted into the body once hollow guidewire 120 is in place. In another example, hollow guidewire 120 may be on the order of 175 centimeters in length, suitable for guiding treatment catheters of the rapid-exchange, telescope, multi-exchange and/or zipper types.

At guidewire proximal end 124, hollow guidewire 120 includes features to aid in the control of inflation fluid 132 through guidewire central lumen 122. At guidewire distal end 126, hollow guidewire 120 includes one or more balloon-inflation side ports 136 to allow inflation and deflation of inflatable balloon 130. At guidewire distal end 126, guidewire central lumen 122 may be plugged or capped. Additional structures may be added to guidewire distal end 126, such as a metallic coil or other flexible tubular element to assist in guiding hollow guidewire 120 through the body. Radiopaque markers and other indicia for determining the location of inflatable balloon 130 may also be added onto hollow guidewire 120.

Inflatable balloon 130 is attached near guidewire distal end 126. Inflatable balloon 130 is, in one example, a spherical or cylindrical elastic membrane having proximal and distal ends attached to an outside surface of hollow guidewire 120. Inflatable balloon 130 may be inflated and enlarged by filling balloon interior region 134 with a fluid, without leakage either through the elastic membrane material or through the attached proximal and distal ends of inflatable balloon 130. Inflatable balloon 130 may comprise, for example, one or more layers of expandable material such as polyurethane, radiopaque polyurethane material, thermoplastic polyurethane elastomers, aliphatic polyurethanes, aromatic polyurethanes, styrene-ethylene-butylene-styrene (SEBS) block copolymer, low-density polyethylene, polyethylene terephthalate, polyethylene terephthalate glycol, silicone, copolymer of polyurethane and silicone, natural rubber, synthetic rubber, a thermoplastic polyamide, latex, polyethylene, polyisoprene, polyisobutylene, thermoplastic elastomers, an elastomeric material, or combinations thereof. Attachment of inflatable balloon 130 to hollow guidewire 120 may be achieved with a suitable adhesive, heat bonds, mechanical couplers, wire wraps, bands, or other types of balloon attachment techniques. When inflation fluid 132 is pushed into inflation balloon 130, the balloon enlarges in proportion to the amount of the fluid inside. When deployed in the body, inflation balloon 130 is enlarged to fill a region of the vessel and temporarily block flow through the vessel.

To inflate inflatable balloon 130, guidewire central lumen 122 fluidly communicates with balloon interior region 134 through side port 136 in hollow guidewire 120, side port 136 being positioned between central lumen 122 and inflatable balloon 130. Side port 136 may comprise, for example, a hole, a slot, an aperture, or series of holes, slots or apertures in sidewall 162 of hollow guidewire 120 between proximal and distal ends of inflatable balloon 130. Side port 136 allows inflation fluid 132 from central lumen 122 to flow into balloon interior region 134. Inflation fluid 132 may be a saline solution, a contrast fluid, or other suitable liquid for injecting into inflatable balloon 130.

Rotary valve 140 includes a portion of rotary shaft 142 disposed within guidewire proximal end 124. Rotary shaft 142 comprises, for example, a small-diameter wire of stainless steel, nitinol, or other suitably flexible and strong material. Rotary shaft 142 may compnse a polymeric material such as nylon or Teflon® with good flexibility and sealing properties yet with sufficient torsional rigidity to controllably rotate rotary shaft 142 within hollow guidewire 120. In one embodiment, rotary shaft outer surface 144 slidably contacts a portion of guidewire inner surface 128 within guidewire proximal end 124. In one example, rotary shaft 142 includes flat channel 138 formed on a side of rotary shaft distal end 148. As rotary shaft 142 is rotated, one or more inflation holes 160 formed in guidewire sidewall 162 are opened or closed, thereby controlling the flow of inflation fluid 132 through inflation hole 160 and central lumen 122. Hole 160 being closed means being blocked or covered with a movable element of rotary valve 140 to prevent fluid flow through inflation hole 160. When rotary valve 140 is open, fluid is permitted to flow through inflation hole 160 and into or out of guidewire central lumen 122. As rotary shaft 142 is rotated, one or more inflation holes 160 formed in guidewire sidewall 162 are opened or closed, thereby controlling the flow of inflation fluid 132 through inflation hole 160 and central lumen 122. Hole 160 being closed means being blocked or covered with a movable element of rotary valve 140 to prevent fluid flow through inflation hole 160. When rotary valve 140 is open, fluid is permitted to flow through inflation hole 160 and into or out of guidewire central lumen 122. In another example, flat 146 forms channel 138 in rotary shaft distal end 148, as will be described in more detail below.

In one example, rotary valve 140 includes rotary shaft 142 with first portion 150 disposed within guidewire proximal end 124 and second portion 152 disposed outside and proximally adjacent to guidewire proximal end 124. Rotary shaft first portion 150 has a first diameter sized for a light interference and slidable rotating fit within guidewire central lumen 122. Rotary shaft second portion 152 has a second diameter substantially equal to the outer diameter of hollow guidewire 120. A shoulder formed between rotary shaft first and second portions 150, 152 abuts guidewire proximal end 124, providing a positive stop against translation of rotary shaft 142 into hollow guidewire 120. To aid in the smooth delivery and removal of treatment catheters over balloon catheter 110, a relatively smooth, continuous surface is provided between an outer surface of rotary shaft second portion 152 and an outer surface of hollow guidewire 120.

To prevent unwanted axial movement of rotary shaft 142 within hollow guidewire 120, containment groove 154 may be circumferentially disposed about rotary shaft 142. Containment groove 154 may be ground, turned, or otherwise formed into rotary shaft 142. Containment groove 154 may be mated to one or more protrusions 164 extending inwardly from an inner diameter of hollow guidewire 120. The interfitment between containment groove 154 and protrusions 164 allows easy rotation of rotary shaft 142 yet prevents unwanted axial movement of rotary shaft 142 into or out of hollow guidewire 120. Protrusions 164 may be coined, crimped, swaged, stamped, peened, pressed or otherwise formed in hollow guidewire 120. In this arrangement, treatment catheters may be readily slid over the outside of hollow guidewire 120 without binding or catching on the outer surface of hollow guidewire 120 near containment groove 154.

Protrusion 164 may extend fully circumferentially within containment groove 154 to form a seal that reduces or eliminates leakage when inflation fluid 132 is under pressure in guidewire central lumen 122. For example, inflation fluid 132 may be under pressure when rotary valve 140 is open during balloon inflation, or when rotary valve 140 is closed after balloon 130 has been inflated. Leakage of inflation fluid 132 through proximal end 124 of hollow guidewire 120 may also be reduced by close fitment between rotary shaft outer surface 144 and guidewire inner surface 128. In other configurations, a sealing compound such as a silicon gel or a polymeric plug may be incorporated into hollow guidewire 120 or rotary shaft 142 to create a rotating seal that minimizes or eliminates the leakage of inflation fluid 132 through guidewire proximal end 124.

Figure 2A:
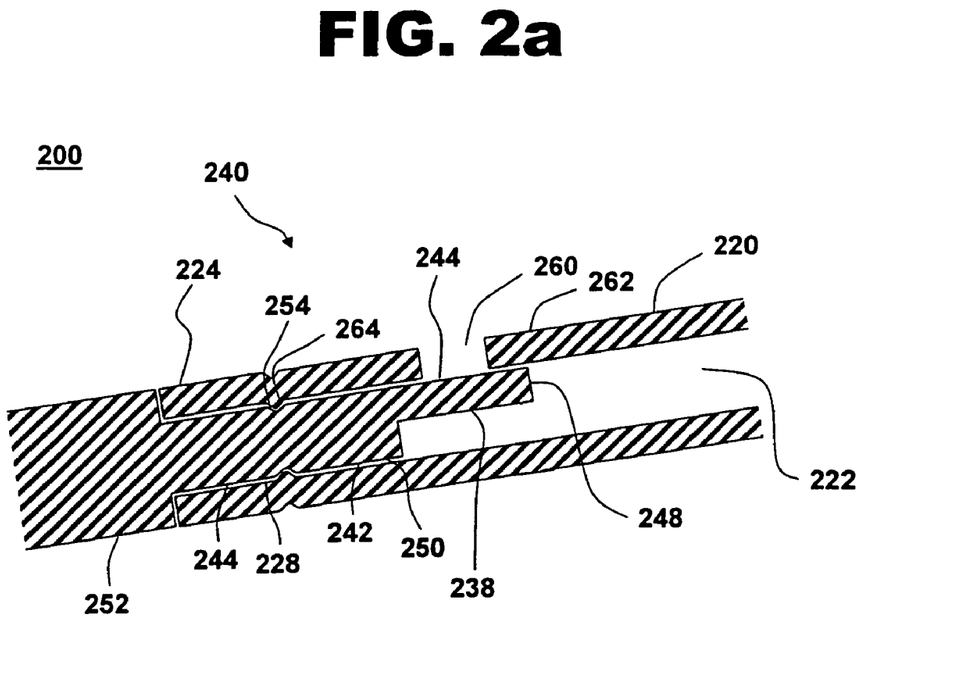
FIG. 2a and FIG. 2b show longitudinal cross-sectional views of a rotary valve for a balloon catheter in a closed position and in an open position, in accordance with one embodiment of the current invention.

FIG. 2a shows a longitudinal cross-sectional view of a rotary valve for a balloon catheter in a closed position, in accordance with one embodiment of the present invention at 200. Rotary valve 240 includes rotary shaft first portion 250 disposed within a portion of guidewire central lumen 222 at guidewire proximal end 224. Rotation of rotary shaft 242 opens and closes rotary valve 240 to control flow of inflation fluid 232 into, out of, and through guidewire central lumen 222. Rotary shaft outer surface 244 has rotatable sliding contact with guidewire inner surface 228 and includes flat channel 238 near rotary shaft distal end 248. Rotary shaft 242 may be rotated within hollow guidewire 220 into one of numerous positions such that flat channel 238 is aligned, misaligned or not aligned with one or more inflation holes 260 formed in guidewire sidewall 262. When flat channel 238 is aligned with hole 260, hole 260 is open to allow inflation fluid to flow into and out of guidewire central lumen 222. When flat channel 238 is misaligned with hole 260, hole 260 is closed by rotary shaft outer surface 244 to prevent inflation fluid from flowing into or out of guidewire central lumen 222. For example, it is desirable to close hole 260 after inflation of balloon 130 to keep balloon 130 inflated while in the body.

Comparable to rotary valve 140, rotary valve 240 has rotary shaft first portion 250 disposed within guidewire proximal end 224. Rotary shaft first portion 250 has a first diameter sized for a light interference and slidable rotating fit within guidewire central lumen 222. Rotary shaft second portion 252 has a second diameter substantially equal to the outer diameter of hollow guidewire 220. A shoulder formed between rotary shaft first and second portions 250, 252 abuts guidewire proximal end 224, providing a positive stop against axial movement of rotary shaft 242 into hollow guidewire 220. To aid in the smooth delivery and removal of treatment catheters over rotary valve 240, a relatively smooth, continuous surface is provided between an outer surface of rotary shaft second portion 252 and an outer surface of hollow guidewire 220.

A containment groove 254 may be circumferentially disposed about rotary shaft 242. Containment groove 254 may be mated to one or more protrusions 264 extending inwardly from an inner diameter of hollow guidewire 220 to prevent axial movement of rotary shaft 242 within hollow guidewire 220.

Figure 2B:
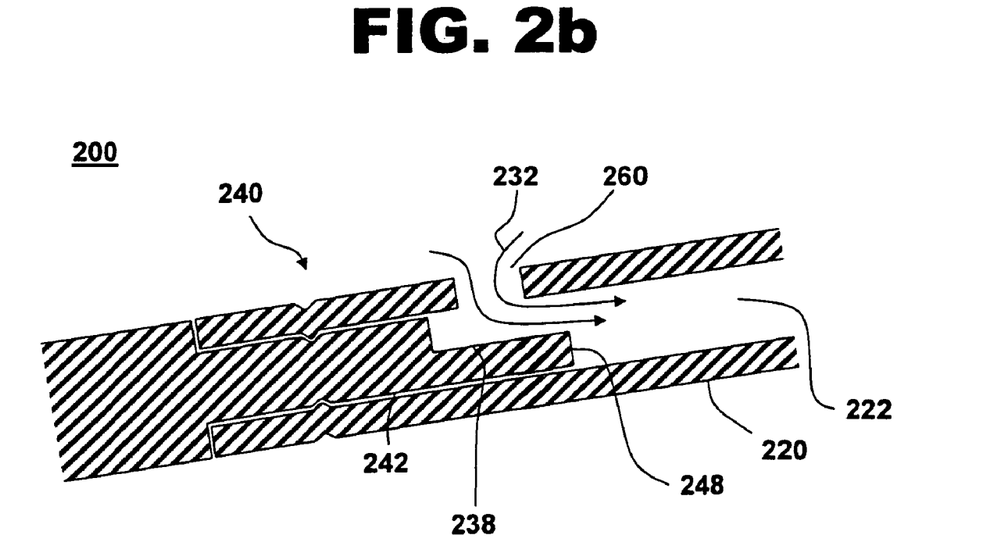

FIG. 2b shows a longitudinal cross-sectional view of the rotary valve of FIG. 2a in an open position, in accordance with one embodiment of the present invention. After rotary shaft 242 has been rotated to open inflation hole 260 in guidewire sidewall 262, inflation fluid 232 may be injected through inflation hole 260 and into guidewire central lumen 222. In reverse fashion, inflation fluid 232 may be withdrawn from guidewire central lumen 222 through open inflation hole 260, as may be done to deflate balloon 130, for example. Flat channel 238 may be included on a side near rotary shaft distal end 248 to allow fluid flow into guidewire central lumen 222 when rotary valve 240 is open.

Indicia, indexing mechanisms and stops may be added to any of the rotary valve embodiments of the invention to aid in accurate, repeatable rotation of the rotary shaft into desired opened or closed positions of the rotary valve. For example, rotary shaft second portion 252 may include visible marks such as dimples, scribe lines or other indicia. A clinician can compare the angular position of inflation hole 260 or other reference indicia on guidewire proximal end 224 with the indicia on rotary shaft second portion 252 to help confirm whether rotary valve 240 is in an open or closed position.

In another example, containment groove 254 may extend only partially around the circumference of rotary shaft 242, and protrusion 264 may engage only a small portion of containment groove 254 to form a rotation stop for rotary shaft 242. In such an arrangement, full rotation against the stop in one direction could place rotary valve 240 in an open position, and full rotation against the stop in the opposite direction could place rotary valve 240 in a closed position.

Figure 3A:
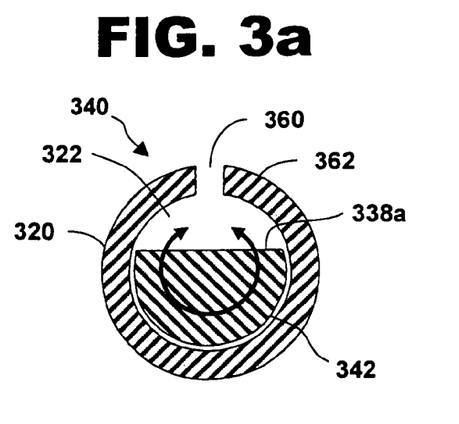
FIG. 3a, FIG. 3b, FIG. 3c and FIG. 3d show transverse cross-sectional views of a rotary valve for a balloon catheter, in accordance with various embodiments of the current invention.
Figure 3B:
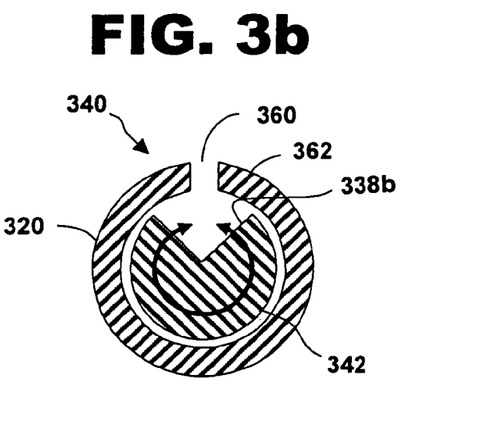
Figure 3C:
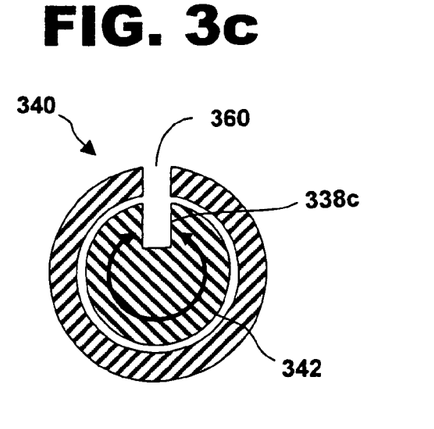
Figure 3D:
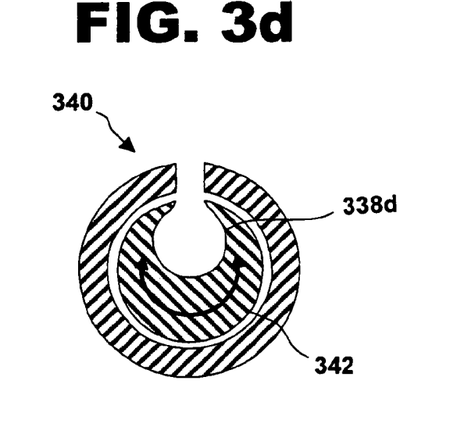

FIG. 3a, FIG. 3b, FIG. 3c and FIG. 3d show cross-sectional views of rotary valve 340 for a balloon catheter, in accordance with various embodiments of the present invention. FIG. 3a illustrates flat channel 338a that is formed by grinding or other cutting operations into a side of rotary shaft 342. When rotary shaft 342 of rotary valve 340 is rotated into the open position shown, flat channel 338a aligns with and opens one or more inflation holes 360 in sidewall 362 of hollow guidewire 320. When rotary shaft 342 is further rotated or rotated in an opposite direction clockwise or counterclockwise, flat channel 338a misaligns, or is not aligned, with one or more inflation holes 360 such that the cylindrical surface of rotary shaft 342 closes inflation hole 360, preventing flow of fluid through inflation hole 360 and into guidewire central lumen 322. In FIG. 3b, v-shaped channel 338b is formed in a side of rotary shaft 342, allowing fluid to flow through inflation hole 360 in sidewall 362 of hollow guidewire 320 when rotary valve 340 is open. Rotary valve 340 is closed by turning rotary shaft 342 until v-shaped channel 338b is not aligned with inflation hole 360 and the cylindrical surface of rotary shaft 342 closes inflation hole 360, preventing fluid from flowing through inflation hole 360. In FIG. 3c, rectangular-shaped channel 338c is formed in a side of rotary shaft 342 to control the flow of fluid through inflation hole 360. In FIG. 3d, eccentrically positioned circular channel 338d is cut or drilled into a side of rotary shaft 342. Other shapes and sizes of channels may be formed into rotary shaft 342 to control the flow of fluid.

Figure 4:
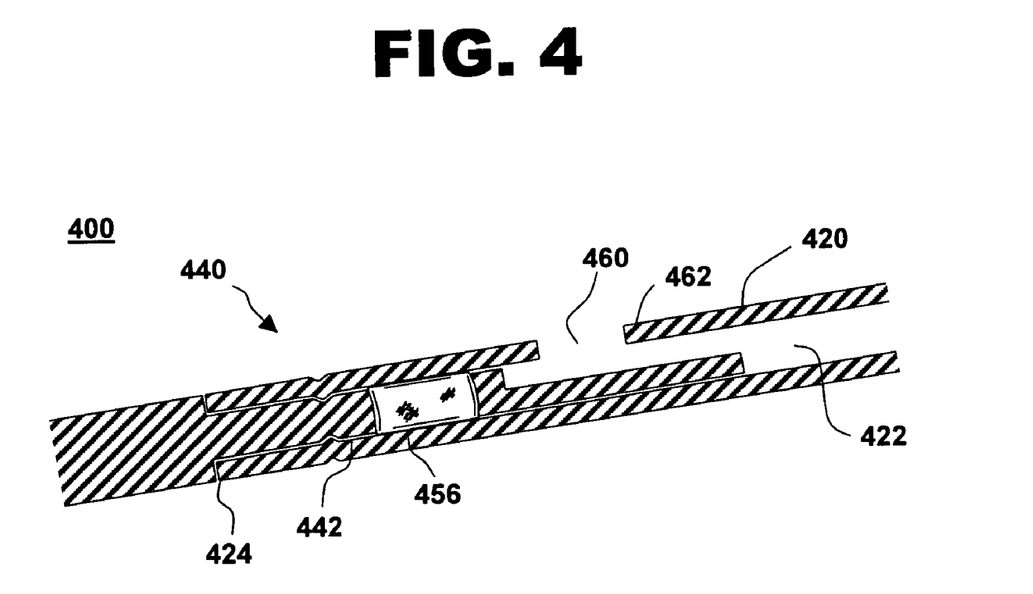
FIG. 4 shows a longitudinal cross-sectional view of a rotary valve for a balloon catheter with a polymeric plug, in accordance with one embodiment of the current invention.

FIG. 4 shows a longitudinal cross-sectional view of rotary valve 440 for a balloon catheter, in accordance with one embodiment of the present invention at 400. Rotary valve 440 includes polymeric plug 456 formed around a portion of rotary shaft 442 within hollow guidewire 420. Polymeric plug 456 provides a fluid seal located between guidewire proximal end 424 and inflation hole 460 formed in guidewire sidewall 462. Polymeric plug 456 reduces or prevents leakage of inflation fluid in guidewire central lumen 422 through guidewire proximal end 424 when rotary valve 440 is in either an open or a closed position.

Polymeric plug 456 may be formed from polyurethane, a silicone, an epoxy, or other suitably wear-resistant and semi-compliant polymer, and provides a snug fit between an outer surface of rotary shaft 442 and an inner surface of hollow guidewire 420. Polymeric plug 466 allows rotary shaft 442 to be turned within hollow guidewire 420, while sealing against fluid leakage from guidewire proximal end 424. Polymeric plug 456 can be shaped and formed to provide a desired degree of rotational resistance, and by itself, can be shaped or formed with a fluid channel.

Figure 5A:
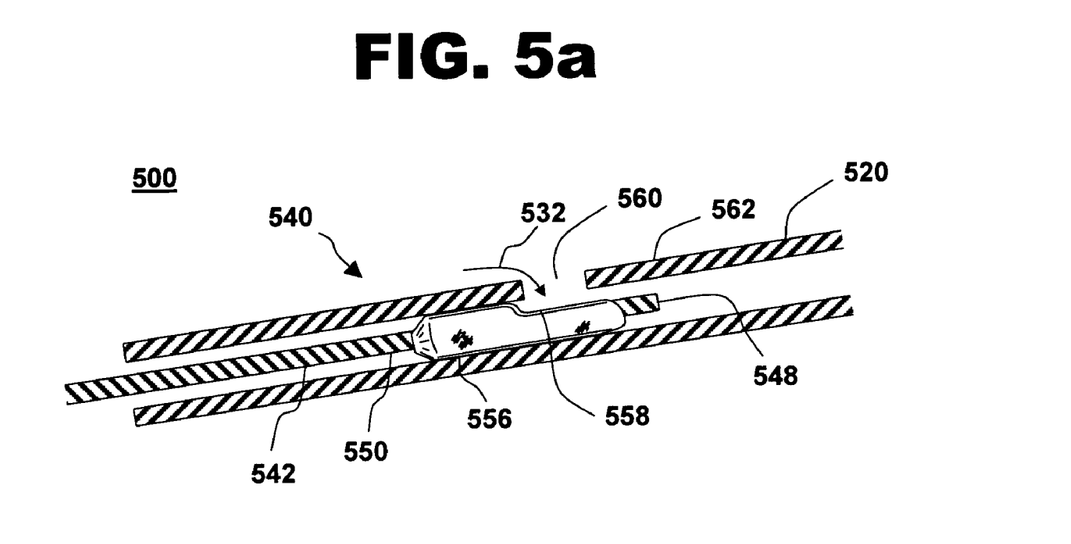
FIG. 5a and FIG. 5b show longitudinal cross-sectional views of a rotary valve with a polymeric plug including a channel formed in a portion of the polymeric plug, in accordance with one embodiment of the current invention.

FIG. 5a shows a longitudinal cross-sectional view of rotary valve 540 including polymeric plug 556 having channel 558 formed in a portion thereof, in accordance with one embodiment of the present invention at 500. Polymeric plug 556, formed near distal end 548 of rotary shaft 542, has channel 558 formed on one side. Channel 558 may be formed, for example, by grinding, scraping, molding, or otherwise shaping polymeric plug 556. When rotary valve 540 is rotated into the open position, polymeric plug 556 with channel 558 allows inflation fluid 532 to flow through one or more inflation holes 560 formed in sidewall 562 of hollow guidewire 520. As can be noted from observing the figure, first portion 550 of rotary shaft 542 can be smaller in diameter than an inner diameter of hollow guidewire 520, without sacrificing the sealing or valving capability of rotary valve 540. It is optional, however, to form a shoulder in rotary shaft 542 where it abuts the proximal end of hollow guidewire 520, providing a positive stop against axial movement of rotary shaft 542 into hollow guidewire 520. In the optional arrangement, a relatively smooth, continuous surface can be provided between an outer surface of rotary shaft 542 and an outer surface of hollow guidewire 520 to aid in the smooth delivery and removal of treatment catheters over rotary valve 540.

Figure 5B:
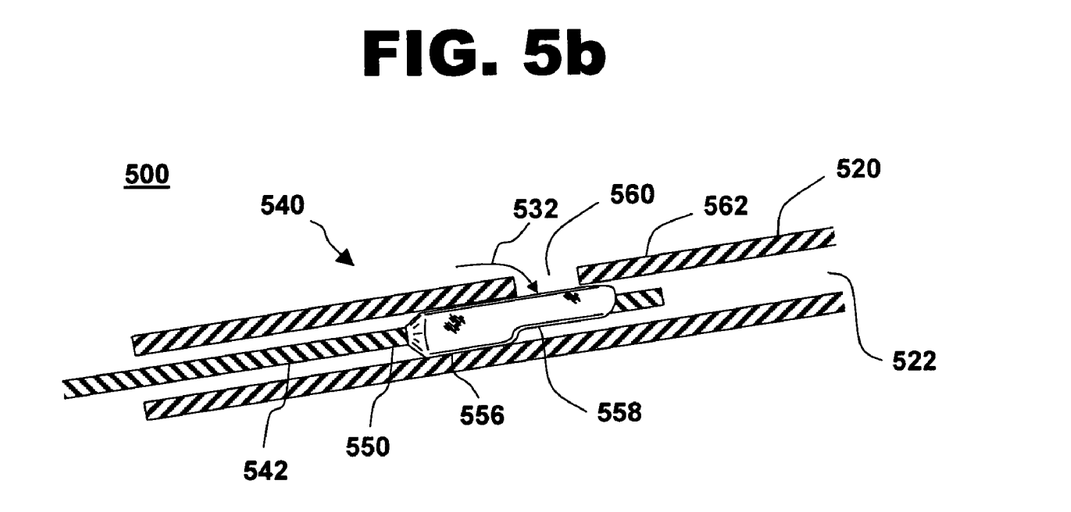

FIG. 5b shows a longitudinal cross-sectional view of rotary valve 540 as in FIG. 5a with polymeric plug 556 in a closed position. Polymeric plug 556 is rotated along with rotary shaft first portion 550 such that channel 558 is not aligned with inflation hole 560 in guidewire sidewall 562. In this closed position, the cylindrical surface of rotary shaft 542 closes inflation hole 560 to block and thereby prevent the flow of inflation fluid 532 into or out of guidewire central lumen 522 through inflation hole 560.

Figure 6:
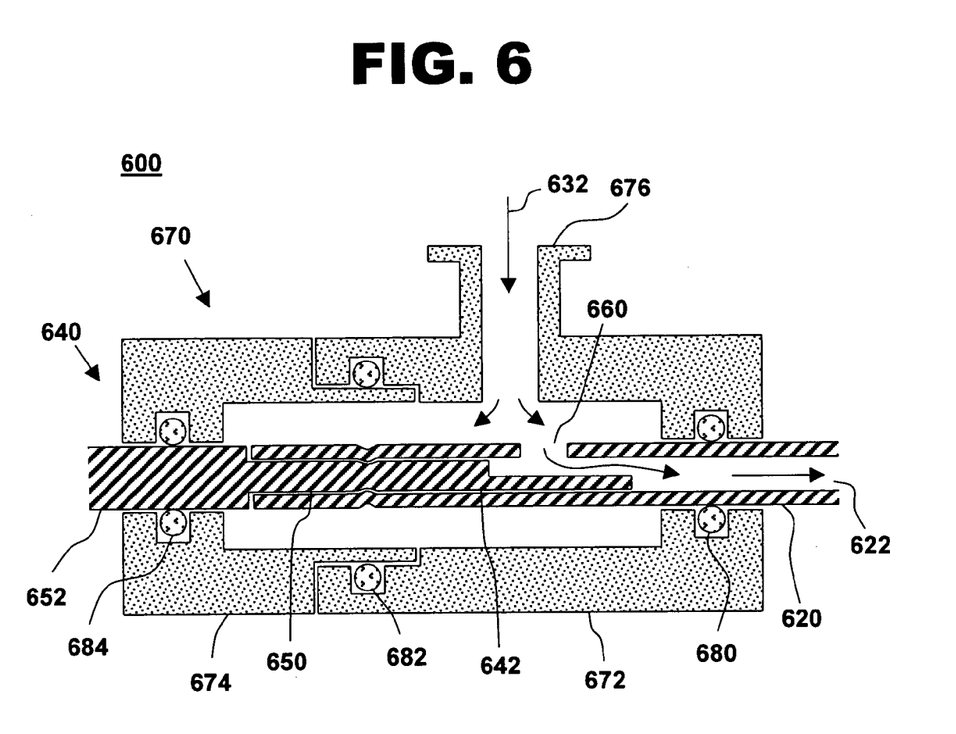
FIG. 6 shows a longitudinal cross-sectional view of a detachable valve actuator for a rotary valve, in accordance with one embodiment of the current invention.

FIG. 6 shows a cross-sectional view of a detachable valve actuator for a rotary valve, in accordance with one embodiment of the present invention at 600. Valve actuator 670, when attached to rotary valve 640, rotates rotary shaft 642 within hollow guidewire 620 to open or close one or more inflation holes 660 in hollow guidewire 620. Detachable valve actuator 670 is operably attached to hollow guidewire 620 and rotary shaft 642. Rotary valve 640 is rotated into an open or a closed position when valve actuator 670 is actuated. As rotary shaft 642 is rotated, inflation hole 660 may be partially opened or partially closed. Valve actuator 670 may comprise first portion 672 to grip hollow guidewire 620 and second portion 674 to grip rotary shaft 642.

A series of elastomeric seals provide gripping and sealing contact between valve actuator 670 and rotary valve 640. Seal 680 of valve actuator first portion 672 grips hollow guidewire 620 distal to inflation hole 660. Seal 684 of valve actuator second portion 674 grips rotary shaft 642. Seal 682 of valve actuator 670 is positioned between first and second valve actuator portions 672, 674 to prevent the leakage of fluids yet allow first portion 672 and second portion 674 of valve actuator 670 to rotate with respect to each other. Seals 680, 682, 684 may comprise O-rings, rectangular rings, elastomeric preforms, elastomeric sealing elements, or other structures that are suitable for gripping and/or sealing.

When valve actuator 670 is attached to rotary valve 640, rotary shaft first and second portions 650, 652 are rotated within hollow guidewire 620 when second portion 674 of valve actuator 670 is rotated with respect to first portion 672 of valve actuator 670. When rotary valve 640 is open, inflation fluid 632 enters inflation fluid port 676 coupled to detachable valve actuator 670 and flows through inflation hole 660 and into guidewire central lumen 622. Inflation fluid port 676 may comprise, for example, a Luer fitting.

Figure 7:
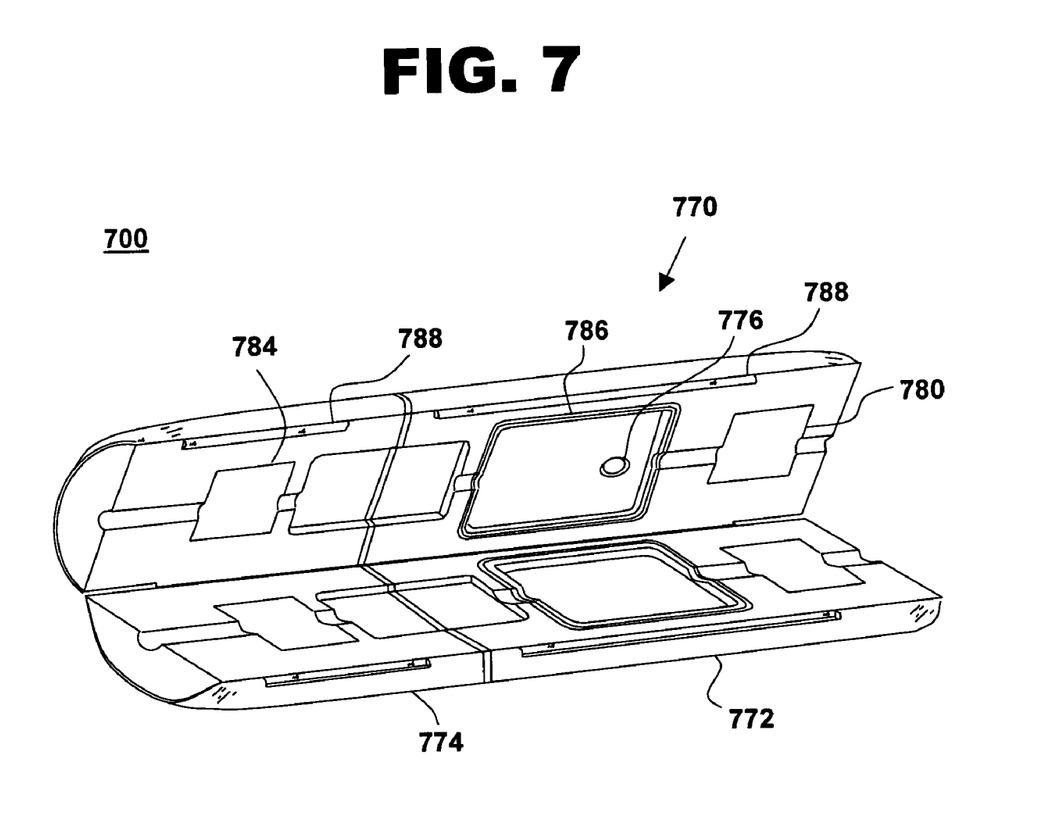
FIG. 7 is an illustration of a valve actuator for a rotary valve, in accordance with one embodiment of the current invention.

FIG. 7 illustrates a valve actuator for a rotary valve, in accordance with one embodiment of the present invention at 700. Valve actuator 770 includes first portion 772 of valve actuator 770 and second portion 774 of valve actuator 770, whereby first portion 772 of valve actuator 770 can be rotated with respect to second portion 774 of valve actuator 770 while being held together. In the illustration, valve actuator 770 is shown in an open position, without a rotary valve or a hollow guidewire.

Various grooves, guides and feed mechanisms allow rotary valve and hollow guidewire to be readily and accurately placed into valve actuator 770. In this illustrated embodiment, latches 788 of valve actuator 770 are used to close and secure valve actuator 770 onto the rotary valve and the hollow guidewire when the rotary valve and hollow guidewire are positioned appropriately. In other versions of valve actuator 770, the rotary valve and hollow guidewire are fed into one end of valve actuator 770 until positioned appropriately to actuate the rotary valve.

Various seals within valve actuator 770 allow the rotary shaft and the hollow guidewire to be gripped and the rotary valve to be actuated. Seal 780 in valve actuator first portion 772 grips onto an outer surface of the hollow guidewire, securing the hollow guidewire to valve actuator 770 and preventing twisting and sliding of the hollow guidewire. Seal 784 in valve actuator second portion 774 grips onto an outer surface of the rotary shaft, securing the rotary shaft to valve actuator 770 and preventing twisting and sliding of the rotary shaft. Seal 786 of valve actuator 770 encloses the inflation hole(s) in the hollow guidewire, allowing fluid to flow through inflation fluid port 776 coupled to valve actuator 770. Seal 786 of valve actuator 770 prevents the fluid from leaking out of valve actuator 770 when the rotary valve is open and fluid is being transported into or out of the hollow guidewire. The seals may have roughened surfaces or other adaptations to aid in gripping the hollow guidewire and the rotary shaft.

Other mechanisms may be coupled to valve actuator 770 to aid in the compression of elastomeric seals against the outside surface of the hollow guidewire and the rotary shaft, such as clamps, tensioners and knobs. Indexing mechanisms and stops may be added to valve actuator 770 to aid in accurate, repeatable rotation of the rotary shaft to open and close the rotary valve. For example, rotary shaft 242 can include a flat (not shown) formed on rotary shaft second portion 252, and protrusion 264 can be a transverse indentation in hollow guidewire 220. Valve actuator 770 may include seals that cooperate with and rely on protrusion 264 and the flat formed on rotary shaft second portion 252 to maintain accurate control over the position of rotary valve 240.

Figure 8:
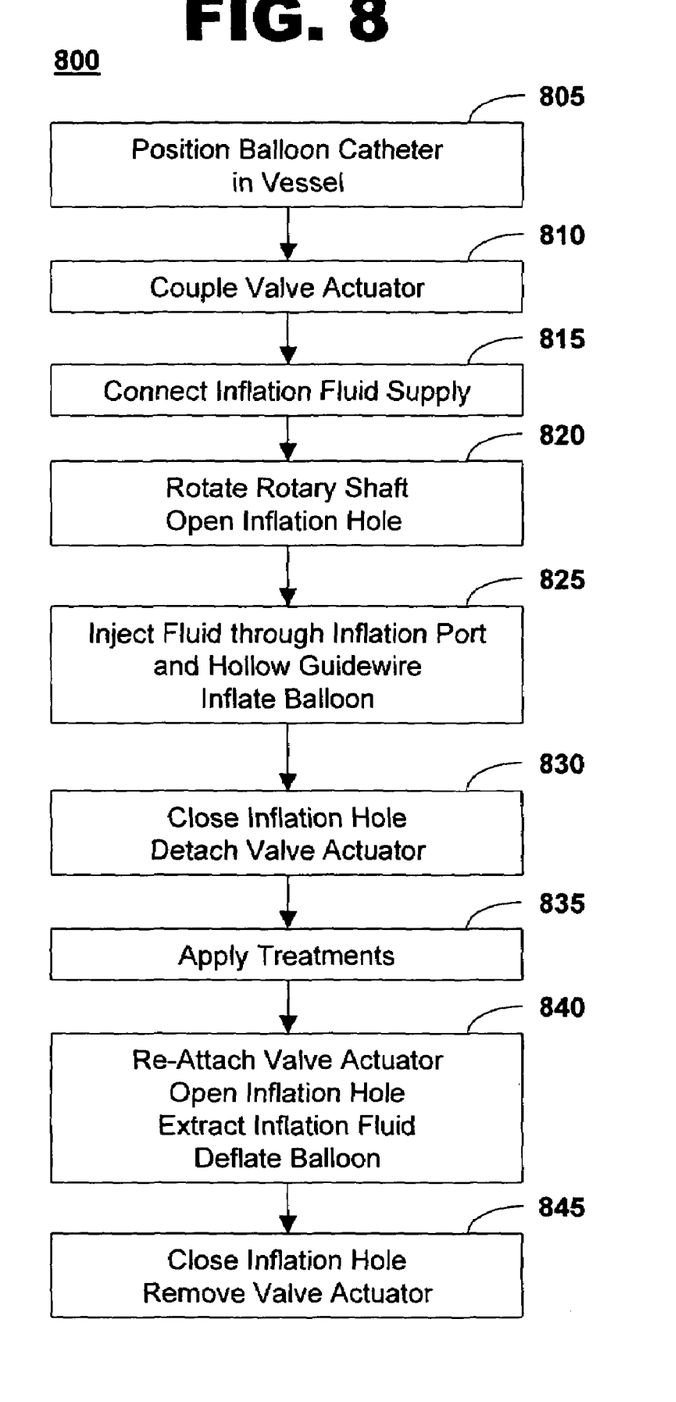
FIG. 8 is a flow diagram of a method for operating a balloon catheter, in accordance with one embodiment of the current invention.

FIG. 8 is a flow diagram of a method for operating a balloon catheter, in accordance with one embodiment of the present invention at 800. Balloon catheter operation method 800 includes various steps to inflate and deflate a balloon near the distal end of the catheter using a rotary valve, and to allow treatments of one or more vascular conditions within the blocked vessel, such as the prevention or correction of various ailments and deficiencies associated with the cardiovascular system, the cerebrovascular system, urogenital systems, biliary conduits, abdominal passageways and other biological vessels within the body.

A balloon catheter with a rotary valve is positioned in a vessel, as seen at block 805. The hollow guidewire with the occlusion or dilation balloon at the distal end is manually manipulated through the vascular system to the desired location for placement of the balloon. For example, a needle puncture is made in the body near the femoral artery, and the hollow guidewire with the inflatable balloon is inserted through the puncture site, through the femoral artery, and into a position within a blood vessel where the balloon is to be inflated. A central lumen with the hollow guidewire and other lumens may be purged with inflation fluid such as diluted contrast fluid or saline solution prior to insertion of the balloon catheter in the body. Prior to the positioning of the occlusion catheter, fluoroscopic contrast fluid may be injected into the blood vessel in order to identify, visualize and verify the location of a stenosis, blockage, or other medical condition within the blood vessel.

A detachable valve actuator is coupled to the rotary shaft of the rotary valve and to the hollow guidewire, as seen at block 810. Depending on the style of valve actuator, the rotary valve and the hollow guidewire may be fed through the valve actuator or sandwiched between two portions of the valve actuator by closing a lid or other coupling mechanism. When an inflation port in a sidewall of the hollow guidewire is correctly placed within the valve actuator, the valve actuator is secured to the hollow guidewire and to the rotary shaft of the rotary valve.

At this point, an inflation fluid supply may be connected to the valve actuator, as seen at block 815. Inflation fluid such as dilute contrast agent or other suitable fluid may be stored in an inflation device and connected to an inflation fluid port, such as a luer fitting on the valve actuator. Various standard procedures can be used to remove air and other gases from the inflation device, lines connected to the valve actuator, and from chambers within the valve actuator.

The rotary shaft of the rotary valve is rotated, as seen at block 820. When the rotary shaft is rotated, a portion of the rotary shaft extending within the hollow guidewire is rotated and an inflation hole in a sidewall of the hollow guidewire is opened, allowing inflation fluid to flow through the valve. Rotations of the rotary shaft may be limited, for example, between 0 degrees and 180 degrees. In another example, the rotary shaft may be rotated clockwise or counterclockwise in a continuous or random manner to open and close the rotary valve.

Inflation fluid is injected through the inflation port, through the inflation hole and into a lumen within the hollow guidewire, as seen at block 825. The occlusion or dilation balloon near the distal end of the hollow guidewire and in communication with the hollow guidewire is inflated with fluid traversing one or more balloon-inflation side ports between the lumen within the hollow guidewire and into an interior region of the inflatable balloon. The balloon is inflated to the desired size. The position and size of the balloon may be monitored, for example, with injections of radiopaque contrast fluid and associated x-ray imaging systems.

When the balloon is inflated to the desired size, the inflation hole is closed, as seen at block 830. A clockwise or counterclockwise movement of the rotary shaft of the rotary valve closes the valve, preventing inflation fluid from flowing through the inflation hole and retaining the balloon in the inflated condition. The valve actuator may be detached and removed.

When the valve actuator has been removed, various treatments can be applied to the vessel, as seen at block 835. For example, a stent-delivery catheter may be inserted over the hollow guidewire and into position within the body prior to deployment of the stent. Other catheters such as an aspiration catheter or an imaging catheter can be positioned over the hollow guidewire and pushed into place.

When the treatments have been completed, the valve actuator is reattached, as seen at block 840. Rotating a rotary shaft of the rotary valve opens the inflation hole, allowing fluid to flow through the inflation hole. Inflation fluid is extracted, and the inflatable balloon deflates. Inflation fluid within the balloon flows through the balloon inflation holes into the central lumen of the hollow guidewire, through the central lumen, through the inflation holes near the proximal end of the hollow guidewire, and out through the inflation port in the valve actuator until the balloon is deflated.

Inflation fluid may be extracted, for example, with an inflation/deflation device, with negative pressure, or by elastic restoring forces within the balloon.

The inflation hole is closed by rotating the rotary shaft of the rotary valve to cover the inflation hole, as seen at block 845. The valve actuator is removed from the hollow guidewire and the rotary valve. The hollow guidewire and the inflatable balloon are then removed from the body.

Variations and alterations in the design, manufacture and use of the balloon catheter and the rotary valve are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vessel in a body, comprising:
   a hollow guidewire having a central lumen;
   an inflatable balloon attached near a distal end of the hollow guidewire;
   an inflation hole formed in a sidewall near a proximal end of the hollow guidewire; and
   a rotary valve including a rotary shaft portion rotatably disposed within the proximal end of the hollow guidewire, the shaft portion comprising a solid round wire having an eccentric channel formed along a side thereof, the channel extending across the inflation hole and being in fluid communication with the central lumen when the valve is open, wherein flow of an inflation fluid through the central lumen of the hollow guidewire and into an interior region of the inflatable balloon is controlled by rotating the rotary shaft of the rotary valve.

2. The system of claim 1 wherein an outer surface of the rotary shaft within the proximal end of the hollow guidewire rotatably contacts a portion of an inner surface of the hollow guidewire.

3. The system of claim 1 wherein the eccentric channel includes one of a flat channel, a v-shaped channel, a rectangular-shaped channel, or a circular channel.

4. The system of claim 1 wherein a first portion of the rotary shaft within the proximal end of the hollow guidewire has a first diameter sized for a rotating fit within an inner diameter of the hollow guidewire, and a second portion of the rotary shaft adjacent to the proximal end of the hollow guidewire has a second diameter substantially equal to an outer diameter of the hollow guidewire.

5. The system of claim 1 further comprising:
   a containment groove circumferentially disposed about the rotary shaft, the containment groove mated to a protrusion extending inwardly from an inner diameter of the hollow guidewire to prevent axial movement of the rotary shaft within the hollow guidewire.

6. The system of claim 1 further comprising:
   a polymeric plug formed around a portion of the rotary shaft within the hollow guidewire, the polymeric plug providing a fluid seal near the proximal end of the hollow guidewire.

7. The system of claim 6 further comprising:
   a channel formed in a portion of the polymeric plug to allow fluid flow into the central lumen of the hollow guidewire when the rotary valve is open.

8. The system of claim 1 further comprising:
   a detachable valve actuator operably attached to the hollow guidewire and the rotary shaft, wherein the rotary valve is rotated into one of an open position or a closed position when the valve actuator is actuated.

9. The system of claim 8 further comprising:
   an inflation fluid port operably coupled to the detachable valve actuator, wherein fluid from an inflation fluid supply connected to the inflation fluid port flows through the central lumen of the hollow guidewire when the rotary valve is open.

* * * * *